US008293255B2

(12) United States Patent
Soula et al.

(10) Patent No.: US 8,293,255 B2
(45) Date of Patent: Oct. 23, 2012

(54) POLYGLUTAMIC ACIDS FUNCTIONALISED BY HISTIDINE DERIVATIVES AND HYDROPHOBIC GROUPS AND THE USES THEREOF, IN PARTICULAR FOR THERAPEUTIC PURPOSES

(75) Inventors: Olivier Soula, Meyzieu (FR); Rémi Soula, Lyons (FR); Olivier Breyne, Lyons (FR)

(73) Assignee: Flamel Technologies (FR)

( * ) Notice: Subject to any disclaimer, the term of this patent is extended or adjusted under 35 U.S.C. 154(b) by 596 days.

(21) Appl. No.: 12/084,368

(22) PCT Filed: Oct. 31, 2006

(86) PCT No.: PCT/FR2006/002443
§ 371 (c)(1),
(2), (4) Date: Oct. 19, 2009

(87) PCT Pub. No.: WO2007/051923
PCT Pub. Date: May 10, 2007

(65) Prior Publication Data
US 2010/0034886 A1 Feb. 11, 2010

(30) Foreign Application Priority Data

Oct. 31, 2005 (FR) ...................................... 05 53302

(51) Int. Cl.
  *A61K 9/10* (2006.01)
  *A61K 9/16* (2006.01)
  *A61K 9/00* (2006.01)
  *A61K 47/32* (2006.01)
  *A61K 47/00* (2006.01)
(52) U.S. Cl. ..................... 424/400; 514/772.6; 514/777; 424/491
(58) Field of Classification Search .................. None
See application file for complete search history.

(56) References Cited

U.S. PATENT DOCUMENTS

| 4,351,337 | A | 9/1982 | Sidman |
| 4,652,441 | A | 3/1987 | Okada et al. |
| 4,888,398 | A | 12/1989 | Bichon et al. |
| 5,449,513 | A | 9/1995 | Yokoyama et al. |
| 5,904,936 | A | 5/1999 | Huille et al. |
| 6,153,193 | A | 11/2000 | Kabanov et al. |
| 6,630,171 | B1 | 10/2003 | Huille et al. |
| 2008/0152675 | A1* | 6/2008 | Pouliquen ..................... 424/400 |

FOREIGN PATENT DOCUMENTS

| FR | 2 801 226 | 5/2001 |
| FR | 2 910 318 | * 8/2007 |
| WO | WO 99/61512 | 12/1999 |
| WO | WO 03/104303 | 12/2003 |
| WO | WO 2004/013206 | 2/2004 |
| WO | WO 2004/060968 | 7/2004 |

OTHER PUBLICATIONS

Akiyoshi, et al., "Self-Assembled Hydrogel Nanoparticle of Cholesterol-Bearing Pullulan as a Carrier of Protein Drugs: Complexation and Stabilization of Insulin," *J. Control, Release*, 1998 vol. 54, pp. 313-320.
H.R. Kricheldorf, "α-Amino Acid N-Carboxy Anydrides and Related Heterocycles," *Springer-Verlag, Berlin Heidelberg 1987.*
W.C. Shen, "Acid-sensitive Dissociation Between Poly(lysine) and Histamine-modified Poly(glutamate) as a model for drug-releasing from carriers in Endosomes," *Biochimica et Biophysica Acta*, 1990, vol. 1034, pp. 122-124.
Yang et al., "Histidine Conjugated Poly(amino acid) Derivatives as the Novel Intracellular Delivery Carrier of an Anticancer Drug," *Controlled Release Society, 32nd Annual Meeting*, Miami, Jun. 2005, #254, 2 pages.
Seo et al., "Phase Transition Behavior and Particle Size Change of pH-sensitive Imidazole&C18-grated Poly(asparagine)s," *Controlled Release Society, 32nd Annual Meeting*, Miami, Jun. 2005, #361, 2 pages.
Bikram et al., "Biodegradable Polyethylene glycol)-co-poly(L-lysine)-g-histidine Multiblock Copolymers for Nonviral Gene Delivery," *Macromolecules*, 2004, vol. 37, pp. 1903-1916.
Laustsen et al., "The Complete Amino Acid Sequence of Human Placental Oxytocinase", *Biochimica et Biophysica Acta*, 1997, vol. 1352, No. 1, pp. 1-17.
Sen et al., "Role of Histidine Interruption in Mitigating the Pathological Effects of Long Polyglutamine Stretches in SCA1: A Molecular Approach," *Protein Science*, 2003, vol. 12, pp. 953-962.
Oppenheim et al., "The Primary Structure and Functional Characterization of the Neutral Histidine-rich Polypeptide from Human Parotid Secretion" *The Journal of Biological Chemistry*, 1986, vol. 261, No. 3, pp. 1177-1182.
Jaworek et al., "Effects of Analogs of (pyro)Glu-His-Gly-OH on Food Consumption and Gastric Acid Secretion in Rats," *Life Science*, 1984, vol. 34, No. 26, pp. 2597-2603.
Shimura et al., "Fluorescence-labeled Peptide pI Markers for Capillary Isoelectric Focusing," *Analytical Chemistry*, 2002, vol. 74, No. 5, pp. 1046-1053.

* cited by examiner

*Primary Examiner* — Robert A Wax
*Assistant Examiner* — Jeffrey T Palenik
(74) *Attorney, Agent, or Firm* — Patton Boggs LLP

(57) ABSTRACT

The invention relates to novel biodegradable materials based on modified polyamino acids and suitable, in particular, for vectoring active substance(s) (AS). Said invention also relates to novel pharmaceutical, cosmetic, dietary or plant protective compositions which are based on said polyamino acids.
The aim of said invention is to provide a novel polymer raw material usable for vectoring the AS and capable to optimally meet all specification in this area: biocompatibility, biodegradability, ability to become easily associated with many active substances or to solubilize them and to release said active substances in vivo. The aim is attained to 30 carbon atoms.
Said polyglutamates modified by histidine derivatives are soluble with pH lower than 5 and are easily and economically convertible into active substance vectorization particles which are able to form stable aqueous colloidal suspensions. On the contrary, said modified polyglutamates are insoluble in water with a physiological pH (7.4), and thereby have to be precipitated on an injection site in the case of a subcutaneous injection.

27 Claims, No Drawings

POLYGLUTAMIC ACIDS FUNCTIONALISED BY HISTIDINE DERIVATIVES AND HYDROPHOBIC GROUPS AND THE USES THEREOF, IN PARTICULAR FOR THERAPEUTIC PURPOSES

CLAIM FOR PRIORITY

This application is a National Stage application of PCT Application No. PCT/FR2006/002443, filed Oct. 31, 2006, which claims priority to the French Application No. FR 0553302, filed Oct. 31, 2005, both of which are herein incorporated by reference in their entirety.

The present invention relates to novel biodegradable materials based on copolyamino acids of use in particular for the vectorization of active principle(s) (APs).

The invention is also targeted at novel pharmaceutical, cosmetic, health-food or plant-protection compositions based on these modified polyamino acids. These compositions can be of the type of those which make possible the vectorization of AP and which are preferably provided in the form of emulsions, micelles, particles, gels, implants or films.

The APs under consideration are advantageously biologically active compounds which can be administered to an animal or human organism by the oral, parenteral, nasal, vaginal, ocular, subcutaneous, intravenous, intramuscular, intradermal, intraperitoneal, intracerebral or buccal route and the like.

The APs to which the invention more particularly but non-limitingly relates are proteins, glycoproteins, peptides, polysaccharides, lipopolysaccharides, oligo- or polynucleotides, and organic molecules. However, cosmetic products or plant-protection products, such as herbicides, insecticides, fungicides, and the like, may also be concerned.

In many cases there exists a need, in the field of the vectorization of active principles, in particular medicinal active principles:

to protect them from decomposition (hydrolysis, enzymatic digestion, and the like),
and/or to control their rate of release, in order to maintain a therapeutic level over a defined period of time,
and/or to convey them (while protecting them) to the site of action.

Several types of polymers have been studied for these purposes and some are even available commercially. Mention may be made, for example, of polymers of the polylactic, polylactic/glycolic, polyoxyethylene/oxypropylene, polyamino acid or polysaccharide type. These polymers constitute starting materials which make it possible to manufacture, for example, bulk implants, microparticles, nanoparticles, vesicles, micelles or gels. Apart from the fact that these polymers have to be suitable for the manufacture of such systems, they also have to be biocompatible, non-toxic, non-immunogenic and economic and they have to be able to be easily eliminated from the body and/or to be biodegradable. With regard to the latter aspect, it is moreover essential for the biodegradation in the body to generate non-toxic products.

Various patents or patent applications or scientific papers are mentioned below by way of illustration of the prior art relating to polymers employed as starting materials for the preparation of AP vectorization systems.

U.S. Pat. No. 4,652,441 describes polylactide microcapsules encapsulating the hormone LH-RH. These microcapsules are produced by preparing a water-in-oil-in-water emulsion comprising an aqueous internal layer comprising the hormone, a substance (gelatin) which fixes the latter, an oily polylactide layer and an aqueous external layer (polyvinyl alcohol). The release of the AP can take place over a period of more than two weeks after subcutaneous injection.

U.S. Pat. No. 6,153,193 describes compositions based on amphiphilic micelles of poly(oxyethylene)/poly(oxypropylene) for the vectorization of anticancer agents, such as adriamycin.

Akiyoshi et al. (J. Controlled Release, 1998, 54, 313-320) describe pullulans which are rendered hydrophobic by grafting cholesterol and which form nanoparticles in water. These nanoparticles, which are capable of reversibly complexing with insulin, form stable colloidal suspensions.

U.S. Pat. No. 4,351,337 describes amphiphilic copolyamino acids based on leucine and on glutamate which can be used in the form of implants or of microparticles for the controlled release of active principles. The release of the active principles can take place over a very long period of time depending on the rate of decomposition of the polymer.

U.S. Pat. No. 4,888,398 describes polymers based on polyglutamate or polyaspartate and optionally polyleucine with pendent groups of alkyloxycarbonylmethyl type placed randomly on the polyamino acid chain. These polyamino acids, grafted by side groups, e.g. methoxycarbonylmethyl groups, can be used in the form of biodegradable implants comprising an AP for prolonged release.

U.S. Pat. No. 5,904,936 describes nanoparticles obtained from a polyleucine/polyglutamate block polymer which are able to form stable colloidal suspensions and which are capable of joining together spontaneously with biologically active proteins without denaturing them. The latter can subsequently be released in vivo in a controlled manner over a long period.

U.S. Pat. No. 5,449,513 describes amphiphilic block copolymers comprising a polyoxyethylene block and a polyamino acid block, for example poly(β-benzyl-L-aspartate). These polyoxyethylene/polybenzylaspartate polymers form micelles which are capable of encapsulating hydrophobic active molecules, such as adriamycin or indomethacin.

Patent application WO-A-99/61512 describes polylysines and polyornithines functionalized by a hydrophobic group (palmitic acid connected to the polylysine or -ornithine) and a hydrophilic group (polyoxyethylene). These polymers, for example polylysine grafted with polyoxyethylene and palmitoyl chains, form, in the presence of cholesterol, vesicles capable of encapsulating doxorubicin or DNA. These polymers based on polylysines are cationic in physiological medium.

U.S. Pat. No. 6,630,171 of the Applicant Company describes block or random poly(sodium glutamate)-poly(methyl, ethyl, hexadecyl or dodecyl glutamate) polymers suitable for forming stable colloidal suspensions and capable of spontaneously joining together with biologically active proteins without denaturing them. The latter can subsequently be released in vivo in a controlled manner over a long period. These amphiphilic linear copolyamino acids are modified by the presence of a hydrophobic alkyl side chain. These alkyl groups are covalently grafted to the polymer via an ester functional group. These polymers are anionic in physiological medium.

In the same field, the Applicant Company has described, in several patent applications, polymers based on polyglutamate (anionic polymers) with related concepts.

Application WO-A-03/104303 describes anionic polyamino acids functionalized by α-tocopherol.

Application WO-A-2004/013206 describes anionic polyamino acids comprising hydrophobic groups, wherein these groups are connected to the polymer via a joint comprising two amide functional groups and more specifically via a spacer of lysine or ornithine type.

Application WO-A-2004/060968 describes polyamino acids functionalized by at least one oligoamino acid group based on leucine and/or isoleucine and/or valine and/or phenylalanine.

The paper by W. C. Shen, Acid-sensitive dissociation between poly(lysine) and histamine-modified poly (glutamate) as a model for drug-releasing from carriers in endosomes, *Biochim. Biophys. Acta*, 1034 (1): 122-124, 1990, describes a polyglutamate functionalized by 40% of histamine. However, no hydrophobized polyglutamate backbone is described. Furthermore, the polymer enlarged upon precipitates between pH 4 and 5 and is soluble at physiological pH. Only the application targeted at forming complexes with a pH-sensitive polylysine is enlarged upon. These complexes are based on electrostatic interactions. Specifically, at physiological pH, the polyglutamate-histamine/polylysine complex is formed, whereas it decomposes at pH 4-5, value of the pH in the endosome.

More recently, Kim et al. have described polyaspartates modified by imidazole derivatives and carrying fatty amines ($C_{18}NH_2$), Controlled Release Society, 32nd annual meeting, Miami, June 2005, #254 and #361. First of all, these polymers are based on polyaspartates composed of a mixture of $\alpha$ form and $\beta$ form. Furthermore, in the communication #254, the histidine is grafted via the acid functional group, which results in a polymer being obtained which exhibits pendent group amines and thus in a polymer being obtained which is cationic and soluble at physiological pH. In the communication #361, the graft is not a histidine derivative but an imidazole derivative, 1-(3-aminopropylimidazole). A few papers describe polylysines functionalized by histidine derivatives. The paper by M. Bikram et al., Biodegradable Poly(ethylene glycol)-co-poly(L-lysine)-g-histidine Multiblock Copolymers for Nonviral Gene Delivery, Macromolecules, 37:1903-1916, 2004 describes the coupling of N-dimethylhistidine to a co-polyethylene glycol-polylysine via the pendent amines of the lysine. These polymers are employed in gene therapy strategies and are thus used to combine with DNA. The role of the histidine is to promote transfection in the cell, this amino acid being cationic in the endosome. Polymer/DNA separation is thus facilitated by electrostatic repulsion in the endosome. These polymers are cationic at neutral pH.

Thus, even if many technical solutions have been developed and provided in the prior art for the vectorization of medicinal active principles, the answer to all the requirements is difficult to obtain and remains able to be improved. More specifically, the invention relates to biodegradable polyamino acids which can be converted into colloidal nano- or microparticles for vectorization capable of reversibly joining together with active principles.

In this context, one of the essential objectives of the present invention is to provide novel, linear or branched, amphiphilic copolyamino acids, the aqueous-phase solubility of which is dependent on the pH. It is advantageous to develop polymers which are soluble at acidic pH (pH<6) and insoluble at physiological pH (pH=7.4). These polymers represent an improvement, with respect to those described in the patents or patent applications mentioned above, in terms of vectorization of an active principle, such as a therapeutic protein.

Another essential objective of the present invention is for these polymers to be capable of being used for the vectorization of AP and to make it possible to optimally satisfy all the specifications of the requirements, namely in particular:

ability:
  to easily and economically form stable aqueous colloidal suspensions,
  to easily join together with numerous active principles, and to release these active principles in vivo,
biocompatibility,
biodegradability,
stability to hydrolysis.

This objective, among others, is achieved by the present invention, which relates to polyamino acids comprising glutamic units, wherein at least a portion of these units carry a histidine derivative and wherein at least a portion of these units carry a pendent hydrophobic group (HG), the histidine derivatives and the HGs being respectively identical to or different from one another.

Each polyglutamate according to the invention is thus functionalized by a multiplicity of pendent histidine derivatives and pendent hydrophobic groups (HGs) which are identical to or different from one another.

Within the meaning of the invention, the term "multiplicity" means that the polyglutamate is functionalized by:
  at least 1% of histidine derivatives (molar %, with respect to the glutamic acids) and up to 99%,
  on average, at least two pendent HGs per molecule. It is possible, in accordance with the invention, for the polyglutamic acid to exhibit, in addition to the pendent HGs, HGs fixed to at least one of the ends of the copolymer chains.

Preferably, for at least one of the portions of the glutamic units carrying a histidine derivative, each unit of said portion carries a histidine derivative, the histidine derivatives being identical to or different from one another, and, for at least one of the portions of the glutamic units carrying a pendent hydrophobic group (HG), each unit of said portion carries a pendent hydrophobic group (HG), the HG groups being identical to or different from one another.

Preferably, the histidine derivatives are pendent with respect to the glutamic units. Within the meaning of the invention, the expression "to carry" means that the group carried is pendent, that is to say that said group is a side group with respect to the glutamic units and is a substituent of the carbonyl functional group in the $\epsilon$ position of the glutamic unit which carries it.

According to a preferred form of the invention, the polyglutamate comprises, on average, at least 3 hydrophobic groups (HGs) per copolymer chain.

The polyglutamate also carries histidine derivatives. These groups are preferably bonded to the copolymer via an amide bond.

It is to the credit of the Applicant Company to have developed a novel family of polymers based on polyglutamate and on histidine derivatives which are "pH sensitive", insoluble at physiological pH, functionalized by a multiplicity of hydrophobic groups and capable of forming stable colloidal systems. The ability to modify the solubility of the polymer as a function of the pH can prove to be very effective in extending the release time. PLAGA-type polymers, which are also insoluble under physiological conditions, make it possible to obtain long release times. The advantage of the system presented is due to its biodegradability.

These novel polymers have proved to be particularly well suited to the vectorization of proteins. Furthermore, they are easily degraded, in the presence of enzymes, to give non-toxic catabolites/metabolites (amino acids).

Within the meaning of the invention and throughout the present specification, the terms "association" or "associate" employed to describe the relationships between one or more active principles and the modified polyglutamates mean, in particular, that the active principle or principles are bonded to the polyglutamate(s) in particular via a hydrophobic interaction and/or are encapsulated by the polyglutamate(s).

Advantageously, the polyamino acids according to the invention are, e.g., α-L-glutamate or α-L-glutamic homopolymers.

The histidine derivatives which can be used to functionalize the glutamate units are identical to or different from one another and correspond to an ethyl substituted in the 1 position by an amine and in the 2 position by an imidazole ring. Other substituents can be present on these two positions. These derivatives can, for example, be: histidine esters (such as the methyl ester and the ethyl ester), histidinol and histamine.

These derivatives can also be, for example, histidinamide, the N-monomethyl derivative of histidinamide and the N,N'-dimethyl derivative of histidinamide.

According to a preferred characteristic, the polyamino acids of the invention comprise, on average, at least 3 hydrophobic groups (HGs) per polymer chain.

Advantageously, at least one of the hydrophobic groups HGs is included in a hydrophobic graft comprising at least one spacing joint (or unit) (spacer) which makes it possible to connect the hydrophobic group HG to a polyglutamate chain (for example, a polyglutamate backbone main chain). This joint can comprise, e.g., at least one direct covalent bond and/or at least one amide bond and/or at least one ester bond. For example, the joint can be of the type of those belonging to the group comprising in particular: "amino acid" units other than the constituent monomeric unit of the polyglutamate, derivatives of aminoalcohols, derivatives of polyamines (for example diamines), derivatives of polyols (for example diols) and derivatives of hydroxy acids.

The grafting of the HGs to the polyglutamate chain can involve the use of HG precursors capable of being bonded to the polyglutamate chain.

The precursors of the HGs are in practice, and without this being limiting, chosen from the group comprising alcohols and amines, it being possible for these compounds to be easily functionalized by a person skilled in the art. The grafting of the HGs is explained in more detail below in the description of the process for obtaining the modified polyamino acids according to the invention.

According to a preferred characteristic, the hydrophobic group HG of the hydrophobic graft comprises from 8 to 30 carbon atoms.

These hydrophobic groups HGs are advantageously and carefully selected from the group comprising:
linear or branched $C_8$ to $C_{30}$ alkyls which can optionally comprise at least one unsaturation and/or at least one heteroatom,
$C_8$ to $C_{30}$ alkylaryls or arylalkyls which can optionally comprise at least one unsaturation and/or at least one heteroatom,
and $C_8$ to $C_{30}$ (poly)cyclic compounds which can optionally comprise at least one unsaturation and/or at least one heteroatom.

The joints which form, with the HGs, hydrophobic grafts can be di-, tri- or tetravalent joints (indeed even pentavalent and more). In the case of a divalent joint, the hydrophobic graft comprises a single HG group, whereas a trivalent joint confers a bifid nature on the hydrophobic graft, that is to say that the graft exhibits two HG "paws". Mention may be made, as examples of trivalent joints, of, inter alia, "amino acid" units, for example "glutamic acid", or polyol residues, for example glycerol. Thus, two advantageous but nonlimiting examples of hydrophobic grafts comprising bifid HGs are dialkylglycerols and dialkyl glutamates.

The hydrophobic groups HGs can, for example, be derived from groups chosen from the group comprising:
octanol, dodecanol, tetradecanol, hexadecanol, octadecanol, oleyl alcohol, tocopherol and cholesterol.

Preferably, the backbone of the polyglutamate according to the present invention comprises α-L-glutamate and/or α-L-glutamic acid units.

More preferably still, the polyglutamates according to the invention correspond to one of the following general formulae (I):

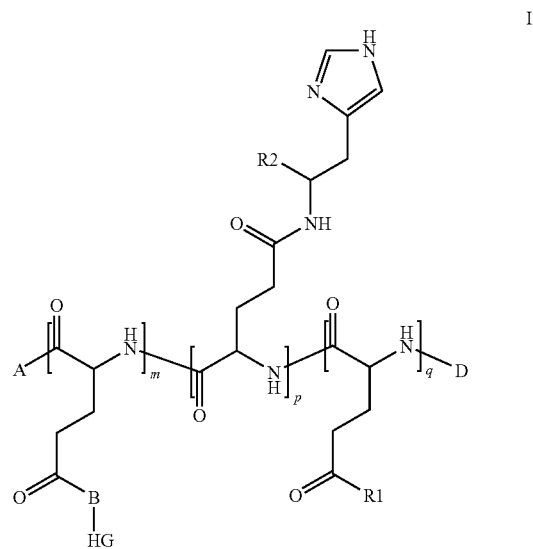

in which:
A independently represents:
an NHR group in which R represents an H, a linear $C_2$ to $C_{10}$ or branched $C_3$ to $C_{10}$ alkyl or a benzyl,
a terminal amino acid unit bonded via the nitrogen, the acid functional group(s) of which is (are) optionally modified by an amine or an alcohol corresponding to the definitions NHR and OR respectively;
B is a divalent, trivalent or tetravalent bonding group preferably chosen from the following radicals:
—O—, —NH—, —N—($C_1$ to $C_5$)alkyl-, an amino acid residue (preferably of a natural amino acid), a diol, a triol, a diamine, a triamine, an aminoalcohol or a hydroxy acid comprising from 1 to 6 carbon atoms;
D represents an H, a linear $C_2$ to $C_{10}$ or branched $C_3$ to $C_{10}$ acyl group or a pyroglutamate;
the hydrophobic groups (HGs) each represent, independently of one another, a radical chosen from:
linear or branched $C_8$ to $C_{30}$ alkyls which can optionally comprise at least one unsaturation and/or at least one heteroatom (preferably O and/or N and/or S), or
$C_8$ to $C_{30}$ alkylaryls or arylalkyls which can optionally comprise at least one unsaturation and/or at least one heteroatom (preferably O and/or N and/or S), or $C_8$ to $C_{30}$ (poly)cyclic compounds which can optionally comprise at least one unsaturation and/or at least one heteroatom (preferably O and/or N and/or S);

R1 represents ethanolamine bonded via the amine or an OX radical in which X represents an H or a cationic entity preferably selected from the group comprising:
metal cations advantageously chosen from the subgroup comprising:
sodium, potassium, calcium and magnesium;
organic cations advantageously chosen from the subgroup comprising:
amine-based cations,
oligoamine-based cations,
polyamine-based cations (polyethyleneimine being particularly preferred),
cations based on amino acid(s) advantageously chosen from the category comprising lysine- or arginine-based cations,
and cationic polyamino acids advantageously chosen from the subgroup comprising polylysine and oligolysine;

R2 represents an alkyl ester, preferably an ethyl ester, a BHG ester, a $CH_2OH$ group (histidinol), H (histamine) or a $C(O)NH_2$ (histidinamide), $C(O)NHCH_3$ or $C(O)N(CH_3)_2$ group;

m, p and q are positive integers;

(m)/(m+p+q) is defined as the molar degree of grafting of the hydrophobic groups HGs and varies from 1 to 50 molar %, provided that each copolymer chain has, on average, at least 3 hydrophobic grafts;

(p)/(m+p+q) is defined as the molar degree of grafting of the histidine groups and varies from 1 to 99 molar %;

(m+p+q) varies from 10 to 1000, preferably between 30 and 500;

(q)/(m+p+q) varies from 0 to 98 molar %.

Preferably, the hydrophobic groups HGs are arranged randomly.

Furthermore, it is preferable for the molar degree of grafting of hydrophobic units of the polyglutamates according to the invention to be between 2 and 100% and preferably between 5 and 50%, provided that each polymer chain has, on average, at least 3 hydrophobic grafts.

The ratio (p)/(m+p+q) of the polyglutamates according to the invention means that they can comprise from 1 to approximately 99 molar % of groups comprising an imidazole ring.

Preferably, the polyamino acids as described above are capable of precipitating at physiological pH.

The ratio (q)/(m+p+q) of the polyglutamates according to the invention means that they can comprise from 0 to approximately 98 molar % of carboxylic, carboxylate or hydroxyethylglutamine functional groups.

According to another noteworthy characteristic of the invention, the polymers according to the invention have a molar mass lying between 2000 and 200 000 g/mol and preferably between 5000 and 100 000 g/mol.

According to an alternative form, the polyglutamates according to the invention can carry at least one graft of polyalkylene (preferably ethylene) glycol type bonded to a glutamate unit.

Naturally, the invention also covers mixtures of modified polyamino acids as defined above.

In a noteworthy fashion, the polyglutamates of the invention are capable of being used in several ways depending on the nature of the hydrophobic groups and the degree of polymerization of the polyglutamate. The methods for forming a polymer for the encapsulation of an active principle in the various forms targeted by the invention are known to a person skilled in the art. For further details, reference is made, for example, to these few particularly relevant references:

"*Microspheres, Microcapsules and Liposomes; Vol. 1. Preparation and Chemical Applications*", edited by R. Arshady, Citus Books, 1999. ISBN: 0-9532187-1-6.

"*Sustained-Release Injectable Products*", edited by J. Senior and M. Radomsky, Interpharm Press, 2000. ISBN: 1-57491-101-5.

"*Colloidal Drug Delivery Systems*" edited by J. Kreuter, Marcel Dekker, Inc., 1994. ISBN: 0-8247-9214-9.

"*Handbook of Pharmaceutical Controlled Release Technology*", edited by D. L. Wise, Marcel Dekker, Inc., 2000. ISBN: 0-8247-0369-3.

These polyglutamates modified by histidine derivatives are in addition extremely advantageous owing to the fact that they disperse in water at a pH of less than 5 (for example in the presence of acid) to give colloidal suspensions or solutions and that they precipitate at physiological pH (7.4), either by addition of a base or by dispersion in a solution at neutral pH. Precipitation should thus in all probability occur at the site of injection during subcutaneous injection. Furthermore, these polyglutamates (in or not in the form of particles) can easily associate or encapsulate active principles, such as proteins, peptides or small molecules. The preferred implementation is that described in U.S. Pat. No. 6,630,171 of the Applicant Company, which consists in dispersing the copolymer in water and in incubating the solution in the presence of an active principle (AP). This colloidal solution of vectorization particles composed of the polyglutamates according to the invention can subsequently be filtered through a 0.2 μm filter and then directly injected into a patient.

Independently of the fact that the microparticulate form of the polymer according to the invention is preferred, the copolymers of the invention, in the neutral or ionized form, can more generally be used alone or in a liquid, solid or gel composition and in an aqueous or organic medium.

It should be understood that the residual carboxyl functional groups of the modified polyglutamate are either neutral (COOH form) or ionized (COO⁻ anion), depending on the pH and the composition. In aqueous solution, the countercation can be a metal cation, such as sodium, calcium or magnesium, or an organic cation, such as triethanolamine, tris(hydroxymethyl)aminomethane or a polyamine, such as polyethyleneimine.

Likewise, the imidazole ring of the histidine derivative is either neutral ($C_3H_3N_2$) or cationic ($C_3H_4N_2^+$), depending on the pH and the composition.

The copolymers of the invention are obtained, for example, by methods known to a person skilled in the art. First of all, it should be remembered that the most widely used technique for obtaining polyamino acids of α type is based on the polymerization of N-carboxyamino acid anhydrides (NCA), described, for example, in the paper "*Biopolymers, 1976, 15, 1869*" and in the work by H. R. Kricheldorf, "*alpha-Amino acid N-carboxy Anhydrides and related Heterocycles*", Springer Verlag (1987). The NCA derivative is preferably NCA-Glu-O-Bz (Bz=benzyl) as the benzyl group can be selectively hydrolysed without affecting other chemical functional groups of the homopolymers or of the hydrophobic group.

A certain number of polymers which can be used according to the invention, for example of poly(α-L-glutamic), poly(α-D-glutamic), poly(α-D,L-glutamate) and poly(γ-L-glutamic) type with variable weights, are available commercially.

Preferably, the copolymers of the invention are synthesized according to two routes. In the first, the histidine derivative (for example ethylhistidine) and the B-HG group (for example dodecylamine) are first of all grafted, simultaneously or sequentially, to a poly(L-glutamic acid). This reaction can take place in a solvent, such as DMF, DMSO or NMP, according to the following scheme.

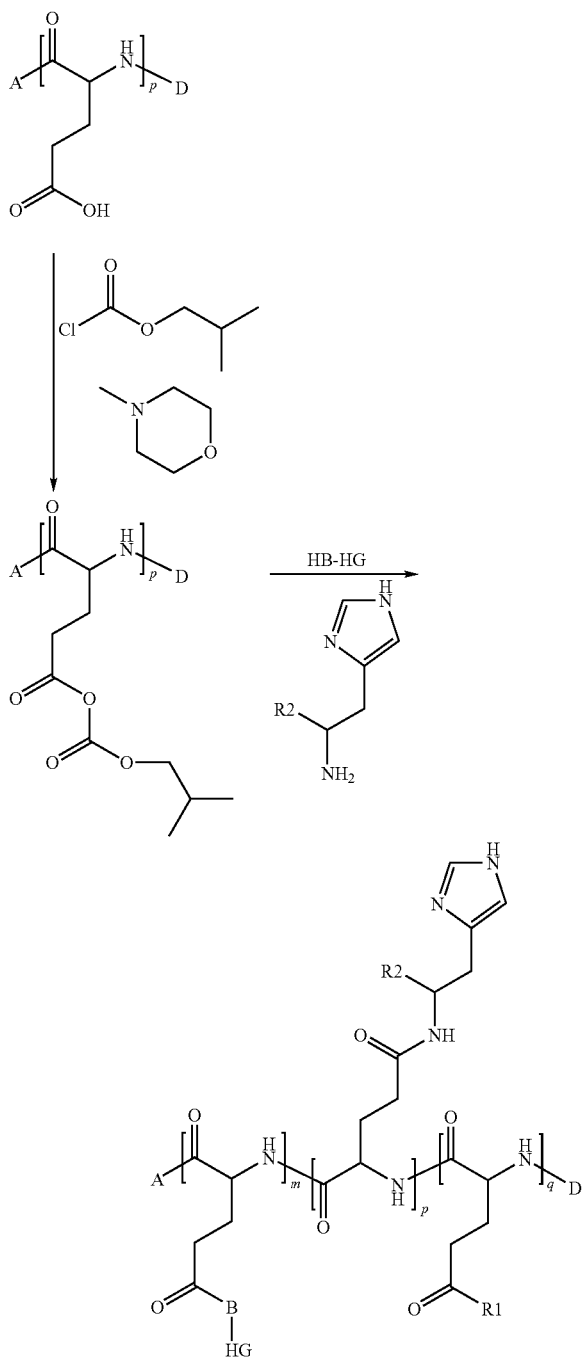

In the above mechanism, when R1 is ethanolamine bonded via the amine, the latter is introduced during the synthesis at the same time as the histidine derivative.

The poly(L-glutamic acid) can be synthesized according to the route described in patent application FR-A-2 801 226. In the case where the HB-HG group is bonded via an ester functional group, it is easier to first graft the B-HG group by a conventional coupling reaction using a carbodiimide, before grafting the histidine derivative.

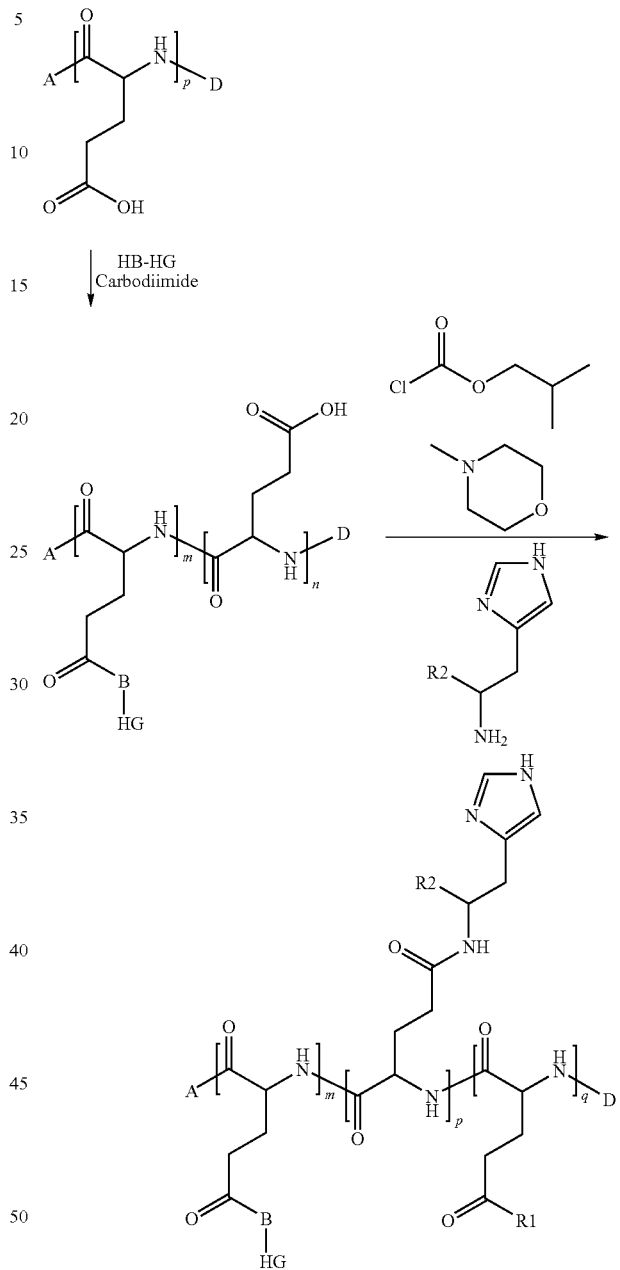

In the above mechanism, when R1 is ethanolamine bonded via the amine, the latter is introduced during the synthesis at the same time as the histidine derivative.

The polymerization chemistry and the reactions for coupling the groups are conventional and well known to a person skilled in the art (see, for example, the patents or patent applications of the Applicant Company mentioned above).

These methods will be better understood through the description of the examples.

It should be observed that the degree of polymerization is defined by the molar ratio of the initiator to that of the monomer.

The coupling of the hydrophobic graft comprising HG with an acid functional group of the polymer is easily carried out by reaction of the polyamino acid in the presence of a carbodiimide as coupling agent and optionally catalyst, such as 4-dimethylaminopyridine, and in an appropriate solvent, such as dimethylformamide (DMF), N-methylpyrrolidone (NMP) or dimethyl sulfoxide (DMSO). The carbodiimide is, for example, dicyclohexylcarbodiimide or diisopropylcarbodiimide. Coupling reagents, such as chloroformates, can also be used for the formation of amide bonds (see, for example, the work by Bodanszky, "Principles of Peptide Synthesis", Springer Verlag, 1984, for examples of coupling agents). The degree of grafting is controlled chemically by the stoichiometry of the constituents and reactants or the reaction time. The hydrophobic grafts functionalized by an amino acid other than that of the polymer are obtained by conventional peptide coupling or by direct condensation by acid catalysis. These techniques are well known to a person skilled in the art.

According to another of its aspects, the invention is targeted at a pharmaceutical, cosmetic, health-food or plant-protection composition, which comprises at least one polyglutamate as defined above and optionally at least one active principle which can be a therapeutic, cosmetic, health-food or plant-protection active principle.

According to an advantageous arrangement of the invention, the active principle is associated with the polyamino acid(s) modified by a histidine derivative by one or more bonds other than (a) covalent chemical bond(s).

The techniques for associating one or more APs with the modified polyamino acids according to the invention are described in particular in U.S. Pat. No. 6,630,171. They consist in incorporating at least one active principle in the liquid medium comprising Vectorization Particles (VP), so as to obtain a colloidal suspension of VPs charged with or associated with one or more active principle(s) AP(s). This incorporation, which results in trapping of AP by the VPs, can be carried out in the following way:
  aqueous dissolution of AP and then addition of the VPs, either in the form of a colloidal suspension or in the form of isolated VPs (lyophilizate or precipitate);
  or addition of AP, either in solution or in the pure or preformulated state, to a colloidal suspension of VP particles optionally prepared at the time of use by the dispersion of dry VPs in an appropriate solvent, such as water.

Preferably, the active principle is a protein, a glycoprotein, a protein bonded to one or more polyalkylene glycol chains (preferably polyethylene glycol (PEG): "PEGylated protein"), a polysaccharide, a liposaccharide, an oligonucleotide, a polynucleotide or a peptide.

According to an alternative form, the active principle is a hydrophobic, hydrophilic or amphiphilic "small" organic molecule. Within the meaning of the present account, a "small" molecule is in particular a small non-protein molecule.

Mention may be made, as examples of APs capable of being associated with the polyamino acids according to the invention, whether or not in the form of (nano- or micro) particles, of:
  proteins, such as insulin, interferons, growth hormones, interleukins, erythropoietin or cytokines;
  peptides, such as leuprolide or cyclosporin;
  small molecules, such as those belonging to the family of the anthracyclines, taxoids or camptothecins;
  and their mixtures.

According to one embodiment, the composition of the invention is in the form of a gel, solution, emulsion, micelles, nanoparticles, microparticles, implant, powder or film.

According to one of its particularly preferred forms, the composition, charged or not charged with active principle(s), is a stable colloidal suspension of polyamino acid nanoparticles and/or microparticles and/or micelles in an aqueous phase.

According to another embodiment, the composition of the invention is in the form of a solution in a biocompatible solvent and can be injected subcutaneously or intramuscularly or into a tumour.

The composition according to the invention, as it is a pharmaceutical composition, can be administered orally, parenterally, nasally, vaginally, ocularly, subcutaneously, intravenously, intramuscularly, intradermally, intraperitoneally, intracerebrally or buccally.

It can also be envisaged for the composition to be in the form of a solution in a biocompatible solvent or a mixture of biocompatible solvents capable of being injected subcutaneously or intramuscularly or into a tumour.

According to another embodiment, the composition can optionally comprise an excipient for the adjustment of the pH and/or of the osmolarity and/or for improving the stability (antioxidants) and/or as antimicrobial agent. These excipients are well known to a person skilled in the art (reference is made to the work: *Injectable Drug Development*, P. K. Gupta et al., Interpharm Press, Denver, Colo., 1999).

According to another alternative form, the composition according to the invention is formulated in such a way that it is capable of forming a deposit on the injection site. The deposition can, for example, be at least partly brought about by a physiological protein present in vivo.

According to another alternative form, the composition according to the invention is characterized in that it comprises polyamino acids of formula I as defined above.

Preferably, this composition is capable of precipitating at physiological pH.

The invention is also targeted at compositions which comprise polyamino acids according to the invention and active principles which are capable of being used for the preparation:
  of medicaments, in particular for oral, nasal, vaginal, ocular, subcutaneous, intravenous, intramuscular, intradermal, intraperitoneal or intracerebral administration, it being possible for the active principles of these medicaments to be in particular proteins, glycoproteins, proteins bonded to one or more polyalkylene glycol chains {for example, PolyEthylene Glycol (PEG); the term then used is "PEGylated" proteins}, peptides, polysaccharides, liposaccharides, oligonucleotides, polynucleotides and hydrophobic, hydrophilic or amphiphilic small organic molecules;
  and/or nutriments;
  and/or cosmetic or plant-protection products.

The invention also relates to a process for the preparation of medicaments, in particular for oral, nasal, vaginaL, ocular, subcutaneous, intravenous, intramuscular, intradermal, intraperitoneal or intracerebral administration, it being possible for the active principles of these medicaments to be in particular proteins, glycoproteins, proteins bonded to one or more polyalkylene glycol chains, peptides, polysaccharides, liposaccharides, oligonucleotides, polynucleotides and hydrophobic, hydrophilic or amphiphilic small organic molecules; and/or nutriments; and/or cosmetic or plant-protection products, this process consisting essentially in employing at least one homopolyamino acid as defined above and/or the composition described above.

This process consists essentially in employing at least one homopolyamino acid as defined above and/or the composition described above.

The invention also relates to a therapeutic treatment method which consists essentially in administering the composition as described in the present account orally, parenterally, nasally, vaginally, ocularly, subcutaneously, intravenously, intramuscularly, intradermally, intraperitoneally, intracerebrally or buccally.

According to a specific alternative form of the invention, this therapeutic treatment method consists essentially in putting the composition as described above in the form of a solution in a biocompatible solvent and in then injecting it subcutaneously or intramuscularly or into a tumour, preferably so that it forms a deposit on the injection site.

The invention will be better understood and its advantages and alternative embodiments will clearly emerge from the examples which follow and which describe the synthesis of the polymers of the invention, their conversion into an AP vectorization system (stable aqueous colloidal suspension) and the demonstration of the ability of such a system to join together with a protein to form pharmaceutical compositions.

EXAMPLES

Example 1

Synthesis of the Polymer (1)

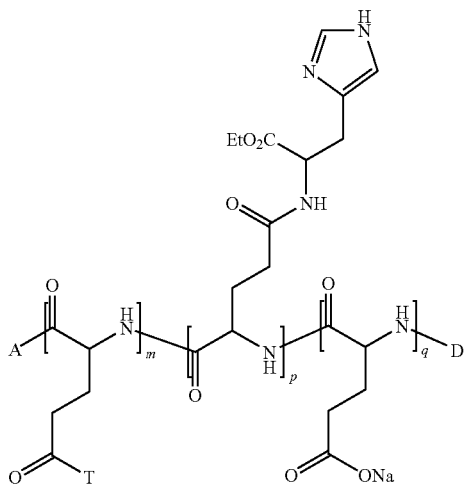

Indices and groups: m=11, p=150, q=59, T=D, L-α-tocopherol (T)

6 g of a poly(glutamic acid) with a degree of polymerization (DP) of 220 randomly grafted with 5% of racemic α-tocopherol are dissolved in 86 ml of DMF by heating at 80° C. This solution is cooled to 0° C. and 5.74 g of isobutyl chloroformate and then 4.26 g of N-methylmorpholine are added. The reaction medium is stirred for 15 minutes while maintaining the temperature at 0° C. At the same time, 20.6 g of histidine ethyl ester dihydrochloride are dissolved in 1.0 l of DMF. 22.5 ml of triethylamine are subsequently added and the solution obtained is then heated at 60° C. for one hour and then cooled to 0° C. The histidine solution is subsequently added to the polymer solution. The reaction medium is stirred for 5 minutes at 0° C. and then for one hour while allowing the temperature to return to ambient temperature. At the end of this time, the reaction medium is first of all quenched by addition of 10 ml of 1N HCl and then diluted in 2.8 l of water to pH 2-3. The final pH is adjusted to 3. The solution is subsequently concentrated to 600 ml on a diafiltration device and then washed against 10 volumes of aqueous saline solution (0.9% NaCl) and 5 volumes of water. The polymer solution is subsequently concentrated to 330 ml with a polymer concentration of 20 mg/ml, i.e. 50% yield. The percentage of histidine ester, determined on the hydrolysed polymer by $^1$H NMR in $D_2O$, is 68%. The Mn (determined by GPC $H_2O$/AcN 65/5) is 11.3 kg/mol in PEO equivalents.

Example 2

Synthesis of the Polymer (2)

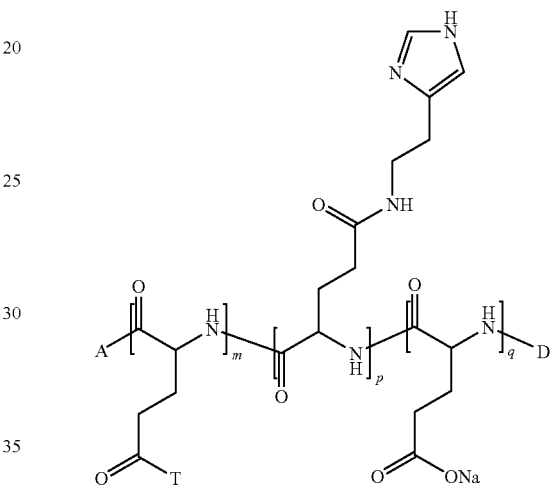

Indices and groups: m=11, p=169, q=40, T=D,L-α-tocopherol (T)

3.5 g of a poly(glutamic acid) with a DP of 220 randomly grafted with 5% of racemic α-tocopherol are dissolved in 50 ml of DMF by heating at 80° C. This solution is cooled to 0° C. and 3.35 g of isobutyl chloroformate and then 2.48 g of N-methylmorpholine are added. The reaction medium is stirred for 15 minutes while maintaining the temperature at 0° C. At the same time, 8.6 g of histamine dihydrochloride are dissolved in 215 ml of DMF. 13.0 ml of triethylamine are subsequently added and the solution obtained is heated at 40° C. for a few minutes and then cooled to 0° C. The histamine solution is subsequently added to the polymer solution. The reaction medium is stirred for 5 minutes at 0° C. and then for one hour while allowing the temperature to return to ambient temperature. At the end of this time, the reaction medium is diluted in 800 ml of water at pH 2-3. The final pH is adjusted to 3. The solution is subsequently concentrated to 500 ml on a diafiltration device and then washed against 10 volumes of aqueous saline solution (0.9% NaCl) and 5 volumes of water. The polymer solution is subsequently concentrated to 230 ml with a polymer concentration of 13.7 mg/ml, i.e. 49% yield. The percentage of histamine, determined on the hydrolysed polymer by $^1$H NMR in $D_2O$, is 77%. The Mn (determined by GPC $H_2O$/AcN 65/35) is 1.5 kg/mol in PEO equivalents.

Example 3

Synthesis of the Polymer (3)

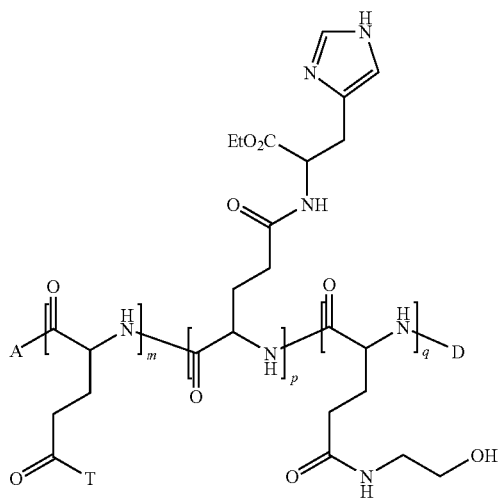

Indices and groups: m=11, p=88, q=121, T=D,L-α-tocopherol (T)

5 g of a poly(glutamic acid) with a DP of 220 randomly grafted with 5% of racemic α-tocopherol are dissolved in 63 ml of NMP by heating at 80° C. This solution is cooled to 0° C. and 4.33 g of isobutyl chloroformate and then 3.67 ml of N-methylmorpholine are added. The reaction medium is stirred for 15 minutes while maintaining the temperature at 0° C. At the same time, 4.28 g of histidine ethyl ester dihydrochloride are dissolved in 43 ml of NMP. 4.66 ml of triethylamine are subsequently added and the solution obtained is stirred at 20° C. for a few minutes and then cooled to 0° C. The histidine solution is subsequently added to the polymer solution. The reaction medium is stirred for 1 h at 0° C., then 4 ml of ethanolamine are added and the temperature is allowed to return to ambient temperature. The reaction medium is stirred for 5 h at 20° C. and then it is diluted in 420 ml of water at pH 2-3. The solution is subsequently diafiltered against 3 volumes of aqueous saline solution (0.9% NaCl) and 8 volumes of water. The polymer solution is subsequently concentrated to a polymer concentration of 56 mg/g. The percentage of grafted histidine ethyl ester, determined on the hydrolysed polymer by $^1$H NMR in $D_2O$, is 40% and the level of ethanolamine is 55%.

Example 4

Synthesis of the Polymer (4)

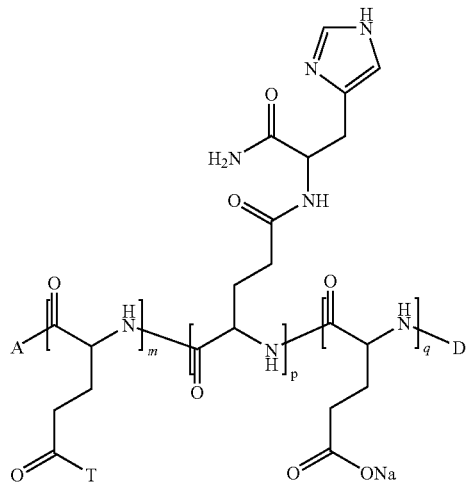

Indices and groups: m=11, p=209, q=0, T=D,L-α-tocopherol (T)

3 g of a poly(glutamic acid) with a DP of 220 randomly grafted with 5% of racemic α-tocopherol are dissolved in 38 ml of NMP by heating at 80° C. This solution is cooled to 0° C. and 2.74 g of isobutyl chloroformate and then 2.2 ml of N-methylmorpholine are added. The reaction medium is stirred for 10 minutes while maintaining the temperature at 0° C. At the same time, 8.65 g of histidinamide dihydrochloride are suspended in 108 ml of NMP. 10.6 ml of triethylamine are subsequently added and the suspension obtained is stirred at 20° C. for a few minutes and then cooled to 0° C. The activated polymer solution is subsequently added to the histidinamide suspension. The reaction medium is stirred for 2 h at 0° C. and then overnight at 20° C. 0.62 ml of 35% HCl is subsequently added, followed by 83 ml of water. The solution obtained is subsequently poured into 500 ml of water at pH 3-4. The solution is subsequently diafiltered against 8 volumes of aqueous saline solution (0.9% NaCl) and 4 volumes of water. The polymer solution is subsequently concentrated to a volume of 300 ml (the polymer concentration of 18 mg/g). The percentage of grafted histidinamide, determined by $^1$H NMR in $D_2O$, is 95%.

Comparative Example 5

The Compound C1 not Functionalized by a Histidine Derivative

The comparative compound C1 is the precursor (in its anionic form) of the polyglutamate modified by a histidine derivative, i.e. the polyglutamate with a DP of 220 randomly grafted with 5% of racemic α-tocopherol. This compound is obtained by the method described in application WO-A-03/104303.

Example 6

Study of Precipitation as a Function of the pH

The results show that the polymers of the invention are soluble at pH values of less than approximately 6 and precipitate when the pH becomes greater than 6, in contrast to the compound C1.

| Polymer | pH ≦ 5 | pH > 6 |
|---|---|---|
| 1 | soluble | insoluble |
| 2 | soluble | insoluble |
| 3 | soluble | insoluble |
| 4 | soluble | insoluble |
| C1 | insoluble | soluble |

Example 7

Measurement of Zeta Potential

The zeta potential of the polymer 1 was measured at two pH values at which the latter is soluble: pH 4 and pH 8, in order to confirm the cationic nature at acidic pH and anionic nature above neutral pH. The values obtained are +53 mV at pH 4 and −37 mV at pH 8. In comparison, the polymer C1 has a zeta potential of −70 mV at neutral pH.

Example 8

Stabilization of a Therapeutic Protein: hGH

The polymer 1 is formulated with human growth hormone (hGH) in the following proportions: polymer 1 50 mg/g+hGH 5 mg/g, pH=5.

hGH has an isoelectric point of 5.4 and is, in principle, insoluble at pH 5. In point of fact, the formulation is clear. The protein is thus stabilized in solution by the polymer 1.

This formulation, injected into a solution buffered at neutral pH (PBS solution), precipitates.

The invention claimed is:

1. A polyamino acid comprising glutamic units, wherein at least a portion of these units carry a histidine derivative and wherein at least a portion of these units carry a pendant hydrophobic group (HG), the histidine derivatives and the HGs being different from one another, and wherein the polyamino acid is soluble at acidic pH and insoluble at physiological pH.

2. The polyamino acid as claimed in claim 1, wherein, for at least one of the portion of the glutamic units carrying a histidine derivative, each unit of said portion carries a histidine derivative, the histidine derivatives being identical to or different from one another, and wherein, for at least one of the portions of the glutamic units carrying a pendant hydrophobic group (HG), each unit of said portion carries a pendent hydrophobic group (HG), the HGs being different from one another.

3. The polyamino acid as claimed in claim 1, wherein the histidine derivatives are pendant with respect to the glutamic units.

4. The polyamino acid as claimed in claim 1, wherein the histidine derivatives are bonded to the glutamic units via an amide bond.

5. The polyamino acid as claimed in claim 2, which are composed of α-L-glutamate or α-L-glutamic homopolymers.

6. The polyamino acid as claimed in claim 1, wherein the histidine derivatives are identical to or different from one another and are chosen from the following groups: histidine esters, histidinol or histamine.

7. The polyamino acid as claimed in claim 1, wherein the histidine derivatives are identical to or different from one another and are chosen from the following groups: histidinamide, the N-monomethyl derivative of histidinamide and the N, N'-dimethyl derivative of histidinamide.

8. The polyamino acid as claimed in claim 1, which comprises, on average, at least 3 hydrophobic groups (HGs) per polymer chain.

9. The polyamino acid as claimed in claim 8, wherein the hydrophobic groups HGs are chosen from:

linear or branched $C_8$ to $C_{30}$ alkyls which can optionally comprise at least one unsaturation and/or at least one heteroatom, $C_8$ to $C_{30}$ alkylaryls or arylalkyls which can optionally comprise at least one unsaturation and/or at least one heteroatom, and $C_8$ to $C_{30}$ (poly)cyclic compounds which can optionally comprise at least one unsaturation and/or at least one heteroatom.

10. The polyamino acid as claimed in claim 1, wherein at least one of the hydrophobic groups HGs is obtained by starting from a precursor chosen from the group comprising: octanol, dodecanol, tetradecanol, hexadecanol, octadecanol, oleyl alcohol, tocopherol and cholesterol.

11. The polyamino acid as claimed in claim 1, which corresponds to one of the following general formula (I):

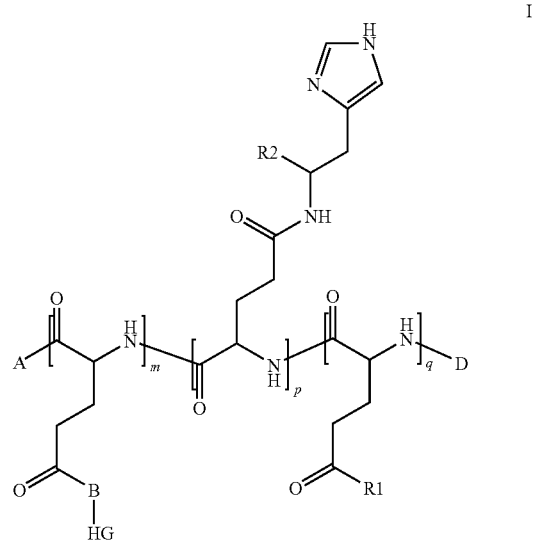

in which:

A independently represents:

an NHR group in which R represents an H, a linear $C_2$ to $C_{10}$ or branched $C_3$ to $C_{10}$ alkyl or a benzyl, a terminal amino acid unit bonded via the nitrogen, the acid functional group(s) of which is (are) optionally modified by an amine or an alcohol corresponding to the definitions NHR and OR respectively;

B is a divalent, trivalent or tetravalent bonding group chosen from the following radicals:

—O—, —NH—, —N—($C_1$ to $C_5$)alkyl-, an amino acid residue, a diol, a triol, a diamine, a triamine, an aminoalcohol or a hydroxy acid comprising from 1 to 6 carbon atoms;

D represents an H, a linear $C_2$ to $C_{10}$ or branched $C_3$ to $C_{10}$ acyl group or a pyroglutamate;

the hydrophobic groups HGs each represent, independently of one another, a radical chosen from:

linear or branched $C_8$ to $C_{30}$ alkyls which can optionally comprise at least one unsaturation and/or at least one heteroatom, or $C_8$ to $C_{30}$ alkylaryls or arylalkyls which can optionally comprise at least one unsaturation and/or at least one heteroatom, or $C_8$ to $C_{30}$ (poly)cyclic compounds which can optionally comprise at least one unsaturation and/or at least one heteroatom;

R1 represents ethanolamine bonded via the amine or an OX radical in which X represents an H or a cationic entity selected from the group comprising:

metal cations chosen from the subgroup comprising: sodium, potassium, calcium and magnesium;

organic cations chosen from the subgroup comprising:
amine-based cations,
oligoamine-based cations,
polyamine-based cations,
cations based on amino acid(s) chosen from lysine- or arginine-based cations, and cationic polyamino acids chosen from polylysine and oligolysine;

R2 represents an alkyl ester, a BHG ester, a $CH_2OH$ group (histidinol), H (histamine) or a $C(O)NH_2$ (histidinamide), $C(O)NHCH_3$ or $C(O)N(CH_3)_2$ group;

m, p and q are positive integers;

(m)/(m+p+q) is defined as the molar degree of grafting of the hydrophobic groups HGs and varies from 1 to 50 molar %, provided that each copolymer chain has, on average, at least 3 hydrophobic grafts;

(p)/(m+p+q) is defined as the molar degree of grafting of the histidine groups and varies from 1 to 99 molar %;

(m+p+q) varies from 10 to 1000;

(q)/(m+p+q) varies from 0 to 98 molar %.

12. The polyamino acid as claimed in claim 1, wherein the hydrophobic groups HGs are arranged randomly.

13. The polyamino acid as claimed in claim 1, which has a molar mass lying between 2000 and 200 000 g/mol.

14. The polyamino acid as claimed in claim 1, which carries at least one graft of polyalkylene glycol type bonded to a glutamate unit.

15. A pharmaceutical, cosmetic, health-food or plant-protection composition, which comprises at least one polyglutamate modified by a histidine derivative as claimed in claim 1.

16. The composition as claimed in claim 15, which comprises at least one active principle.

17. The composition as claimed in claim 16, wherein the active principle is associated with the polyglutamate(s) modified by a histidine derivative by one or more bonds other than (a) covalent chemical bond(s).

18. The composition as claimed in claim 16, wherein the active principle is a protein, a glycoprotein, a protein bonded to one or more polyalkylene glycol chains, a polysaccharide, a liposaccharide, an oligonucleotide, a polynucleotide or a peptide.

19. The composition as claimed in claim 16, wherein the active principle is a hydrophobic, hydrophilic or amphiphilic small organic molecule.

20. The composition as claimed in claim 15, which can be administered orally, parenterally, nasally, vaginally, ocularly, subcutaneously, intravenously, intramuscularly, intradermally, intraperitoneally, intracerebrally or buccally.

21. The composition as claimed in claim 15, which is in the form of a gel, solution, emulsion, micelles, nanoparticles, microparticles, powder or film.

22. The composition as claimed in claim 15, which is a colloidal suspension of nanoparticles and/or microparticles and/or micelles of polyglutamate modified by a histidine derivative in an aqueous phase.

23. The composition as claimed in claim 15, which is in the form of a solution in a biocompatible solvent and which can be injected subcutaneously or intramuscularly or into a tumour.

24. The composition as claimed in claim 23, which is capable of forming a deposit on the injection site.

25. The composition as claimed in claim 15, which comprises polyamino acids according to claim 11.

26. The composition according to claim 1, which is capable of precipitating at physiological pH.

27. A process for the preparation of medicaments, for oral, nasal, vaginal, ocular, subcutaneous, intravenous, intramuscular, intradermal, intraperitoneal or intracerebral administration, wherein the active principles of these medicaments are selected from the group consisting of proteins, glycoproteins, proteins bonded to one or more polyalkylene glycol chains, peptides, polysaccharides, liposaccharides, oligonucleotides, polynucleotides and hydrophobic, hydrophilic or amphiphilic small organic molecules; and/or nutriments; and/or cosmetic or plant-protection products; which consists essentially in employing at least one of the polyamino acids as claimed in claim 1.

* * * * *